United States Patent
Kato

(10) Patent No.: US 10,874,293 B2
(45) Date of Patent: Dec. 29, 2020

(54) ENDOSCOPE DEVICE

(71) Applicant: OLYMPUS CORPORATION, Hachioji (JP)

(72) Inventor: Shuichi Kato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 468 days.

(21) Appl. No.: 15/593,592

(22) Filed: May 12, 2017

(65) Prior Publication Data

US 2017/0251912 A1    Sep. 7, 2017

Related U.S. Application Data

(63) Continuation of application No. PCT/JP2015/051505, filed on Jan. 21, 2015.

(51) Int. Cl.
*A61B 1/04* (2006.01)
*A61B 1/00* (2006.01)
(Continued)

(52) U.S. Cl.
CPC ............ *A61B 1/043* (2013.01); *A61B 1/0005* (2013.01); *A61B 1/00009* (2013.01);
(Continued)

(58) Field of Classification Search
CPC ..... A61B 1/043; A61B 5/0086; A61B 5/0071; A61B 5/0035; A61B 1/0646;
(Continued)

(56) References Cited

U.S. PATENT DOCUMENTS

2006/0066738 A1*  3/2006  Hershey ............... H04N 5/33
                                              348/273
2007/0146512 A1*  6/2007  Suzuki ............... H04N 5/332
                                              348/272
(Continued)

FOREIGN PATENT DOCUMENTS

JP          3962122 B2       8/2007
JP       2014-135535 A       7/2014

OTHER PUBLICATIONS

International Search Report dated Apr. 14, 2015, issued in counterpart of International Application No. PCT/JP2015/051505 w/English Translation (2 pages.

*Primary Examiner* — Ryan N Henderson
(74) *Attorney, Agent, or Firm* — Westerman, Hattori, Daniels & Adrian, LLP

(57) ABSTRACT

An endoscope device includes a light source which generates visible light and excitation light, an imaging unit, an arithmetic unit which generates a visible light image signal according to a first signal and a fluorescence image signal according to a second signal and a third signal, and a switching unit. The imaging unit includes an excitation light cut filter, a first image sensor, and a second image sensor. The excitation light cut filter transmits the visible light and fluorescence, and filters out the excitation light. A plurality of first photodiodes included in the first image sensor generate the first signal according to the visible light and a second signal according to the fluorescence. A plurality of second photodiodes included in the second image sensor generate the third signal according to the fluorescence transmitted through the plurality of first photodiodes.

11 Claims, 12 Drawing Sheets

(51) Int. Cl.
*A61B 1/05* (2006.01)
*A61B 1/06* (2006.01)
*A61B 5/00* (2006.01)

(52) U.S. Cl.
CPC ............ *A61B 1/051* (2013.01); *A61B 1/0638* (2013.01); *A61B 1/0646* (2013.01); *A61B 5/0035* (2013.01); *A61B 5/0071* (2013.01); *A61B 5/0086* (2013.01); *A61B 1/04* (2013.01)

(58) Field of Classification Search
CPC ..... A61B 1/0638; A61B 1/051; A61B 1/0005; A61B 1/00009; A61B 1/04; A61B 5/0059; A61B 5/489; A61B 5/4887; A61B 1/00096; A61B 1/00163; A61B 1/00165; A61B 1/00167; A61B 1/0017; A61B 1/00172; A61B 1/00174; A61B 1/0077; A61B 1/00179; A61B 1/00181; A61B 1/00183; A61B 1/00186; A61B 1/00193; A61B 1/002; A61B 1/041; A61B 1/042; A61B 1/045; A61B 1/05; A61B 1/053; A61B 1/055; A61B 1/0653; H04N 9/09; H04N 9/04553; H04N 9/04563; H04N 9/097; H04N 5/33; H04N 5/332
See application file for complete search history.

(56) References Cited

U.S. PATENT DOCUMENTS

| | | | |
|---|---|---|---|
| 2008/0123097 A1* | 5/2008 | Muhammed | G01J 3/02 356/419 |
| 2009/0065679 A1* | 3/2009 | Tanimoto | H04N 5/33 250/208.1 |
| 2011/0063427 A1* | 3/2011 | Fengler | A61B 1/00186 348/65 |
| 2011/0069868 A1* | 3/2011 | Tsuruoka | A61B 1/05 382/103 |
| 2011/0080506 A1* | 4/2011 | Weng | H04N 9/045 348/254 |
| 2011/0213252 A1* | 9/2011 | Fulghum | A61B 1/00009 600/476 |
| 2012/0307030 A1* | 12/2012 | Blanquart | H01L 24/17 348/76 |
| 2013/0075607 A1* | 3/2013 | Bikumandla | H01L 27/14645 250/332 |
| 2013/0150713 A1* | 6/2013 | Takei | A61B 1/00009 600/431 |
| 2014/0240566 A1* | 8/2014 | Shizukuishi | H01L 27/14634 348/302 |

* cited by examiner

ENDOSCOPE DEVICE

This application is a continuation application based on a PCT International Application No. PCT/JP2015/051505, filed on Jan. 21, 2015. The content of the PCT International Application is incorporated herein by reference.

BACKGROUND OF THE INVENTION

Field of the Invention

The present invention relates to an endoscope device.

Description of Related Art

A diagnosis method of detecting fluorescence from a fluorescence substance accumulated in a lesion such as cancer and determining whether or not there is a lesion from the brightness of a fluorescence image according to the fluorescence is known. For example, a fluorescent substance called indocyanine green (ICG) may be administered to a body of a test target in advance. The fluorescent substance is irradiated with excitation light that excites the fluorescent substance. ICG has an affinity for lesions and is excited in an infrared region and emits fluorescence. An endoscope capable of performing fluorescence observation is capable of performing observation of a fluorescence image in addition to normal observation using a visible light image according to visible light. An endoscope capable of performing fluorescence observation is used for the diagnosis.

For example, Japanese Patent (Granted) Publication No. 3962122 and Japanese Unexamined Patent Application, First Publication No. 2014-135535 disclose an endoscope capable of allowing fluorescence observation. In the first piece of related art disclosed in Japanese Patent (Granted) Publication No. 3962122, a test object is irradiated with visible light and excitation light generated by light source device. The visible light and the excitation light reflected by the test object, and fluorescence from excitation when ICG is irradiated with the excitation light are incident on an objective lens. The objective lens is arranged at a distal end portion of an endoscope insertion unit that is inserted into a body cavity. An image guide fiber is arranged in the endoscope insertion unit. A camera head is arranged on a rear end surface of the image guide fiber. Light incident on the camera head from the objective lens via the image guide fiber is separated into visible light, excitation light, and fluorescence by a dichroic mirror. The visible light is detected by a CCD. The excitation light in the mixture of the excitation light and the fluorescence is filtered out by an excitation light cut filter. Only the fluorescence is detected by a CCD different from the CCD that detects the visible light.

In a second related art disclosed in Japanese Patent (Granted) Publication No. 3962122, only visible light is generated by a light source device at the time of imaging with visible light and only excitation light is generated by the light source device at the time of imaging with fluorescence. Visible light reflected by a test object is detected by a CCD at the time of imaging with visible light. At the time of imaging with fluorescence, the excitation light reflected by the test object and the fluorescence excited when ICG is irradiated with the excitation light are incident on an objective lens. The excitation light is filtered out by an excitation light cut filter. Only the fluorescence is detected by the same CCD as a CCD that detects the visible light.

In a third related art disclosed m Japanese Unexamined Patent Application, First Publication No. 2014-135535, a test object is irradiated with visible light and excitation light generated by a light source. The visible light and the excitation light reflected by the test object, and fluorescence excited when ICG is irradiated with the excitation light are incident on a distal, end portion of an endoscope. Excitation light is filtered out by an excitation light cut filter. An imaging device includes a first substrate and a second substrate that have been stacked. The visible light is detected in a first substrate. The visible light is filtered out by a visible light cut filter arranged between the first substrate and the second substrate. Only fluorescence is detected in the second substrate.

SUMMARY OF THE INVENTION

According to a first aspect of the present invention, an endoscope device includes a light source, an imaging unit, an arithmetic unit, and a switching unit. The light source is configured to generate visible light and excitation light. The arithmetic unit is configured to generate a visible light image signal according to a first signal and a fluorescence image signal according to a second signal and a third signal. The switching unit is configured to switch between a first state and a second state. A subject is irradiated with the visible light in the first state. The subject is irradiated with the excitation light in the second state. The imaging unit includes an excitation light cut filter, a first image sensor, and a second image sensor. The excitation light cut filter is configured to transmit the visible light reflected by the subject when the subject is irradiated with the visible light, transmit fluorescence generated when the subject is irradiated with the excitation light, and filter out the excitation light reflected by the subject when the subject is irradiated with the excitation light. The first image sensor includes the plurality of the first photodiodes. The plurality of first photodiodes are configured to generate the first signal according to the visible light transmitted through the excitation light cut filter and the second signal according to the fluorescence transmitted through the excitation light cut filter. The second image sensor includes a plurality of second photodiodes. The plurality of the second photodiodes are configured to generate the third signal according to the fluorescence transmitted through the plurality of first photodiodes.

According to a second aspect of the present invention, in the first aspect, a size of each of the plurality of second photodiodes is larger than a size of each of the plurality of first photodiodes.

According to a third aspect of the present invention, in the second aspect, two or more of the first photodiodes and one of the second photodiodes may overlap each other. The fluorescence transmitted through the two or more of the first photodiodes may be incident on the one of the second photodiodes.

According to a fourth, aspect of the present invention, in the first aspect, the arithmetic unit may be configured to generate the fluorescence image signal by calculating pixel values corresponding to respective regions of the plurality of the second photodiodes according to the second signal and the third signal.

According to a fifth aspect of the present invention, in the first aspect, the arithmetic unit may be configured to generate the fluorescence image signal by calculating pixel values corresponding to respective regions of the plurality of the first photodiodes according to the second signal and third signal.

According to a sixth aspect of the present invention, in the first aspect, the arithmetic unit may be configured to perform a calculation according to at least one of the visible light image signal such that a number of pixels in the fluorescence image signal corresponding to a pixel in the visible light image signal matches when the number of pixels in the fluorescence image signal corresponding to the one pixel in the visible light image signal is different. The arithmetic unit may be configured to superimpose the visible light image signal and the fluorescence image signal after the calculation.

According to a seventh aspect of the present invention, in the sixth aspect, weights of the visible light image signal and the fluorescence image signal when the visible light image signal and the fluorescence image signal are superimposed are changeable.

According to an eighth aspect of the present invention, in the seventh aspect, the arithmetic unit may be configured to determine the weights according to the pixel value of the fluorescence image signal.

According to a ninth aspect of the present invention, in the seventh aspect, the arithmetic unit may determine the weights according to an instruction from a user.

According to a tenth aspect of the present invention, in the sixth aspect, the arithmetic unit may be configured to use the visible light image signal corresponding to an image in which light having a relatively longer wavelength is emphasized when the visible light image signal and the fluorescence image signal are superimposed over each other.

According to an eleventh aspect of the present invention, in the first aspect, the switching unit may be configured to switch from the first state to the second state with a fixed period, and switch from the second state to the first state with the fixed period. A number of frames of imaging performed by the first image sensor and the second image sensor when the endoscope device is in the second state may be the same as a number of frames of imaging performed by the first image sensor when the endoscope device is in the first state.

According to a twelfth aspect of the present invention, in the first aspect, the switching unit may be configured to switch from the first state to the second state with a fixed period, and switch from the second state to the first state with the fixed period. A number of frames of imaging performed by the first image sensor and the second image sensor when the endoscope device is in the second state may be larger than a number of frames of imaging performed by the first image sensor when the endoscope device is in the first state.

According to a thirteenth aspect of the present invention, in the first aspect, the switching unit may be configured to switch from the first state to the second state with a fixed period, and switch from the second state to the first state with the fixed period. A frame length of imaging performed by the first image sensor and the second image sensor when the endoscope device is in the second state may be longer than a frame length of imaging performed by the first image sensor when the endoscope device is in the first state.

According to a fourteenth aspect of the present invention, in the first aspect, a sensitivity of the second image sensor to near-infrared light may be higher than a sensitivity of the first image sensor to near-infrared light.

DETAILED DESCRIPTION OF THE INVENTION

Figure 1:
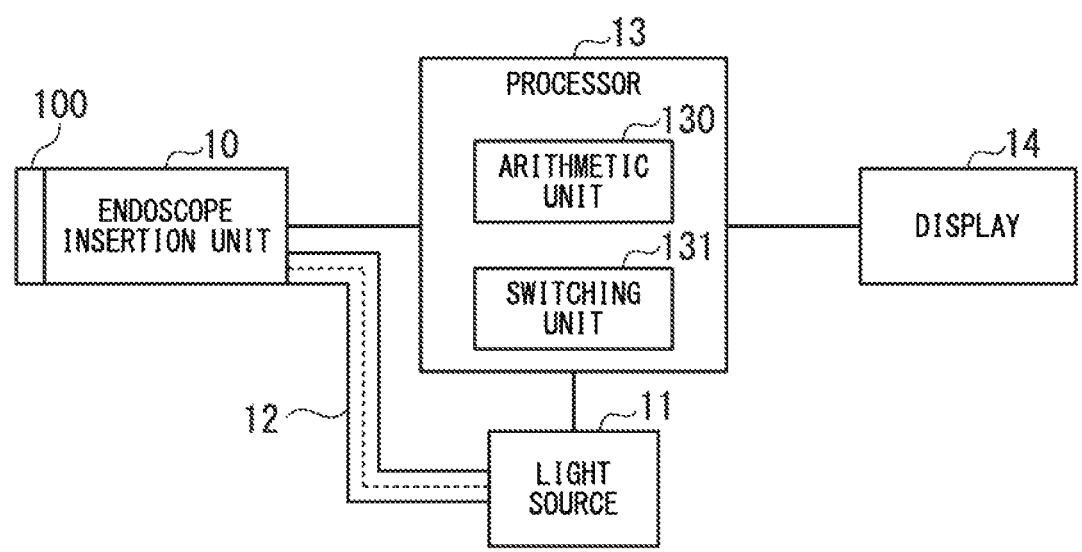
FIG. 1 is a block diagram showing a configuration of an endoscope device according to an embodiment of the present invention.

Embodiments of the present invention will be described with reference to the drawings. FIG. 1 shows a configuration of an endoscope device 1 of an embodiment of the present invention. As shown in FIG. 1, the endoscope device 1 includes an endoscope insertion unit 10, a light source 11, a light guide 12, a processor 13, and a display 14. The endoscope insertion unit 10 includes an imaging unit 100 provided in a distal end portion.

The endoscope insertion unit 10 is inserted into a subject (test object). The light source 11 generates visible light, and excitation light having a wavelength longer than a wavelength of the visible light. For example, the light source 11 includes a first light source that generates the visible light, and a second light source that generates the excitation light. The light source 11 may be arranged in the imaging unit 100. The light guide 12 guides the visible light and the excitation light generated by the light source 11 to the endoscope insertion unit 10.

The processor 13 includes an arithmetic unit 130 and a switching unit 131. The arithmetic unit 130 generates a visible light image signal according to a first signal, and a fluorescence image signal according to a second signal and a third signal. The first signal is a signal that is generated by the imaging unit 100 when the subject is irradiated with the visible light. The second signal and the third signal are signals that are generated by the imaging unit 100 when the subject is irradiated with the excitation light.

The switching unit 131 switches between a first state and a second state. In the first state, the subject is irradiated with the visible light. In the second state, the subject is irradiated with the excitation light. The switching unit 131 controls switching between the visible light and the excitation light and the subject is irradiated with the visible light and the excitation light in a time division manner.

The display 14 displays a visible light image according to the visible light image signal generated by the arithmetic unit 130, and a fluorescence image according to the fluorescence image signal generated by the arithmetic unit 130. The display 14 may display an image according to a superimposed image signal in which the visible light image signal and the fluorescence image signal are superimposed.

Figure 2:
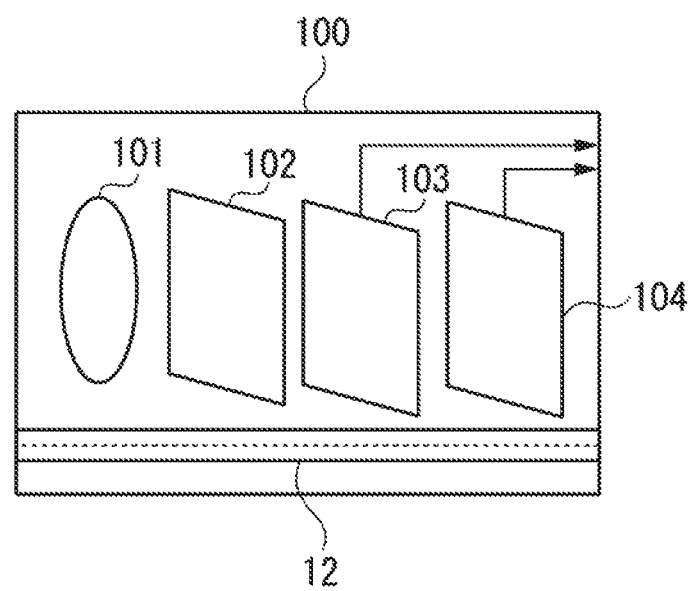
FIG. 2 is a block diagram showing a configuration of an imaging unit according to the embodiment of the present invention.

FIG. 2 shows a configuration of as endoscope imaging unit 100 arranged at a distal end portion of the insertion unit 10. As shown in FIG. 2, the imaging unit 100 includes a lens 101, an excitation light cut filter 102, a first image sensor 103, and a second image sensor 104. Further, the light guide 12 is arranged within the imaging unit 100. The subject is irradiated with the visible light and the excitation light transferred to the imaging unit 100 by the light guide 12 from a distal end surface of the imaging unit 100. The first image sensor 103 and the second image sensor 104 are stacked.

The lens 101 collects light from the test object. The light passing through the lens 101 is incident on the excitation light cut filter 102. The excitation light cut filter 102 transmits the visible light reflected by the subject when the subject is irradiated with the visible light. Further, the excitation light cut filter 102 transmits the fluorescence that is generated when the subject is irradiated with the excitation light. Further, the excitation light cut filter 102 filter out the excitation light reflected by the subject when the subject is irradiated with the excitation light.

The first image sensor 103 includes a plurality of first photodiodes. The plurality of first photodiodes generate a first signal according to the visible light transmitted through the excitation light cut filter 102, and a second signal according to the fluorescence transmitted through the excitation light cut filter 102. The first image sensor 103 performs Imaging to generate a first signal and a second signal. Since the subject is irradiated with the visible light and the excitation light in a time division manner, the first image sensor 103 generates the first signal and the second signal in a time division manner.

The second image sensor 104 includes a plurality of second photodiodes. The plurality of second photodiodes generate a third signal according to the fluorescence transmitted though the plurality of first photodiodes. The second image sensor 104 performs imaging to generate a third signal.

As described above, a plurality of first photodiodes for detecting the visible light and fluorescence and a plurality of second photodiodes for detecting fluorescence are arranged in different image sensors. It is possible to increase the number of the plurality of first photodiodes regardless of the size of the plurality of second photodiodes. It is possible to perform high-resolution detection with the visible light. Since the first image sensor 103 and the second image sensor 104 are stacked, light separation using a dichroic mirror or the like is nest necessary and a small size for the imaging unit 100 can be achieved.

Further, the fluorescence image signal is generated according to the second signal generated by the first image sensor 103 and the third signal generated by the second image sensor 104. It is possible to realize high-sensitivity detection for the fluorescence. It is possible to achieve both a small size for the imaging unit 100 and high accuracy detection of the fluorescence and the visible light.

Figure 3:
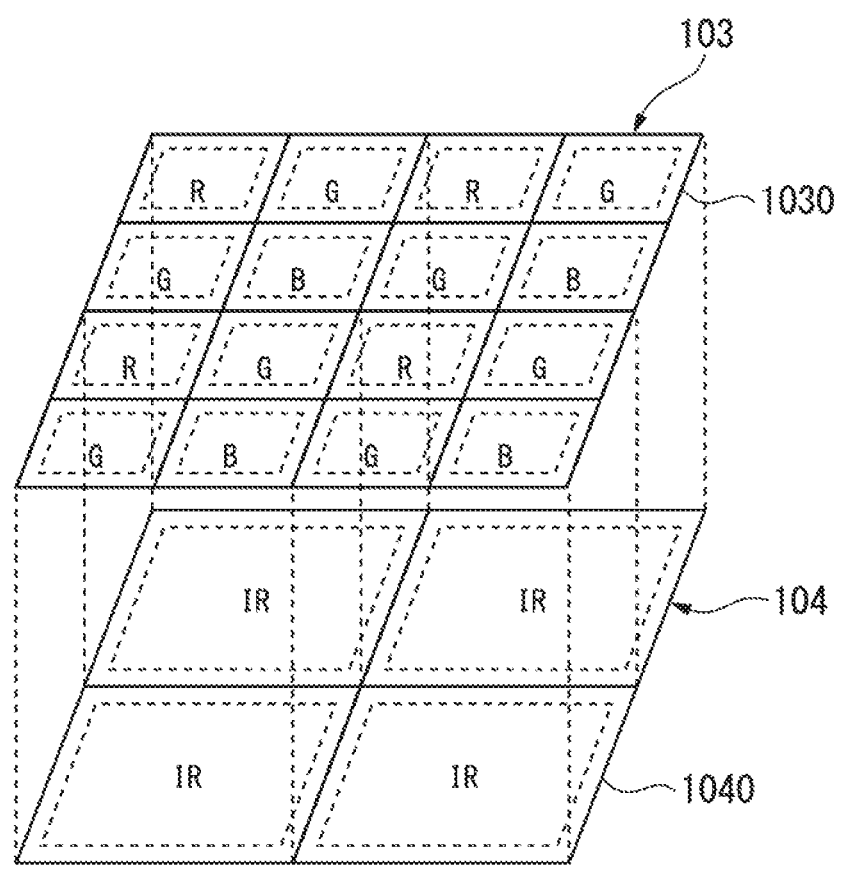
FIG. 3 is a schematic diagram showing a plurality of first photodiodes included in a first image sensor and a plurality of second photodiodes included in a second image sensor in the embodiment of the present invention.

FIG. 3 shows a plurality of first photodiodes 1030 included m the first image sensor 103 and a plurality of second photodiodes 1040 included in the second image sensor 104. As shown in FIG. 3. The first image sensor 103 and the second image sensor 104 are slacked. The plurality of first photodiodes 1030 are arranged in a matrix form. The plurality of second photodiodes 1040 are arranged in a matrix form. Respective sizes (areas) of the plurality of first photodiodes 1030 are different from respective sizes (areas) of the plurality of second photodiodes 1040. The number of the plurality of first photodiodes 1030 is different from the number of the plurality of second photodiodes 1040.

Color filters are arranged on surfaces of the plurality of first photodiodes 1030. For example, an R color filter that transmits light with red (R) wavelengths, a G color filter that transmits light with green (G) wavelengths, and a B color filter that transmits light with blue (B) wavelengths are arranged. The arrangement of the R color filters, the G color filters, and the B color filters is a Bayer array.

The size of each of the plurality of second photodiodes 1040 is larger than the size of each of the plurality of first photodiodes 1030. It is possible to achieve highly sensitive fluorescence detection without compromising a resolution of visible light detection.

Two or more of the first photodiodes 1030 and one of the second photodiodes 1040 overlap. Fluorescence transmitted through two or more of the first photodiodes 1030 is incident on one of the second photodiodes 1040. In FIG. 3, four of the first photodiodes 1030 and one of the second photodiodes 1040 overlap. Further, the fluorescence transmitted through four of the first photodiodes 1030 is incident on one of the second photodiodes 1040. In the second image sensor 104, it is possible to efficiently receive the fluorescence transmitted through the first image sensor 103.

A method of generating a fluorescence image signal will be described. In a first method of generating the fluorescence image signal, the arithmetic unit 130 calculates a pixel value corresponding to each region of the plurality of second photodiodes 1040 according to the second signal and the third signal to generate the fluorescence image signal.

Figure 4:
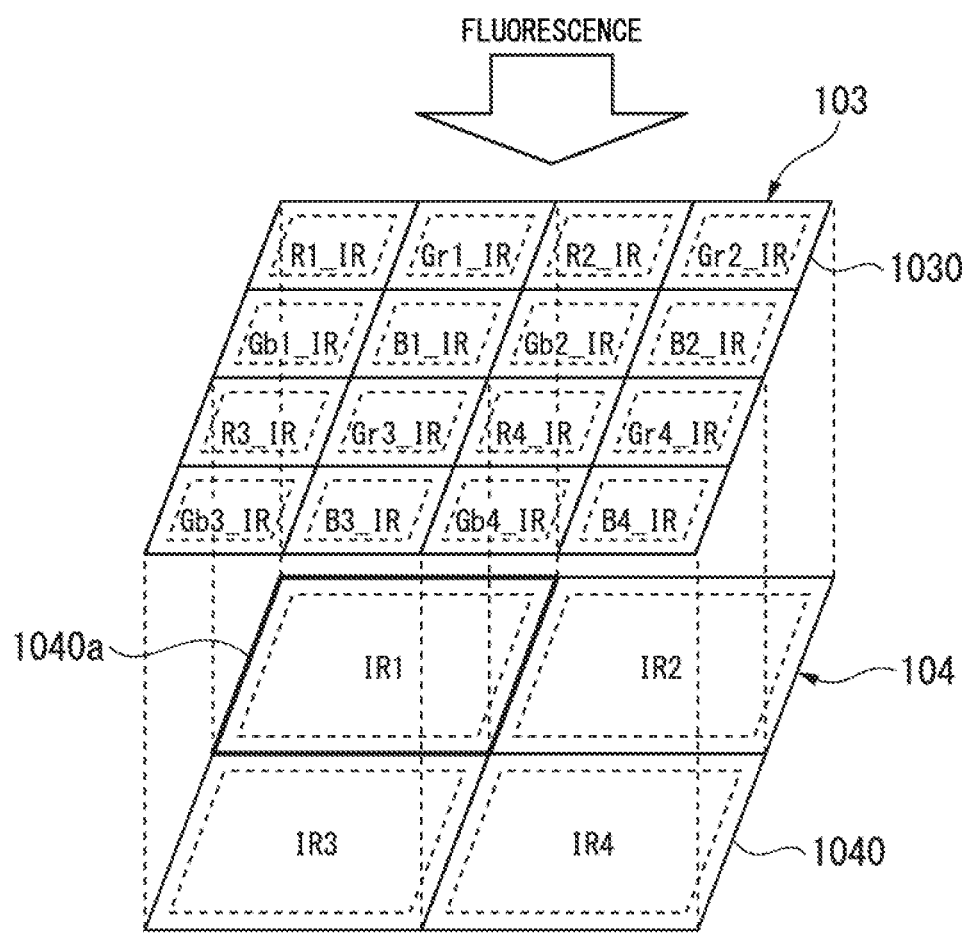
FIG. 4 is a schematic diagram showing a plurality of first photodiodes included in a first image sensor and a plurality of second photodiodes included in a second image sensor in the embodiment of the present invention.

FIG. 4 shows a plurality of first photodiodes 1030 and a plurality of second photodiodes 1040, similar to FIG. 3. When a subject is irradiated with excitation light, fluorescence is generated in the subject. Since the excitation light is filtered out by the excitation light cut filter 102, the fluorescence is incident on the first image sensor 103. A part of the fluorescence is absorbed by the plurality of first photodiodes 1030. The other part of the fluorescence is transmitted through the first image sensor 103 and is incident on the second image sensor 104.

In FIG. 4, sixteen first photodiodes 1030 are shown. Values (pixel values) of second signals generated by the sixteen first photodiodes 1030 are R1_IR to R4_IR, Gr1_IR to Gr4_IR, Gb1_IR to Gb4_IR, and B1_IR to B4_IR, respectively.

In FIG. 4, four second photodiodes 1040 are shown. Values (pixel values) of the third signals generated by the four second photodiodes 1040 are IR1 to IR4, respectively.

For example, the arithmetic unit 130 calculates a pixel value S_IR1 of a fluorescence image signal corresponding to the second photodiode 1040$a$ using Equation (1).

$$S\_IR1 = IR1 + R1\_IR + Gr1\_IR + B1\_IR + Gb1\_IR \quad (1)$$

In Equation (1), a calculation result (R1_IR+Gr1_IR+B1_IR+Gb1_IR) of the second signal corresponding to each of the four first photodiodes 1030 is added to the third signal (IR1) corresponding to the second photodiode 1040a. In Equation (1), the calculation of the second signal is an addition calculation. However, the calculation of the second signal may be a calculation other than the addition calculation. The pixel value of the fluorescence image signal corresponding to the second photodiodes 1040 other than the second photodiode 1040a is calculated through the same calculation as in Equation (1).

In the first method of generating a fluorescence image signal, sensitivity of fluorescence detection is improved.

In a second method of generating the fluorescence image signal, the arithmetic unit 130 calculates the pixel value corresponding to the region of each of the plurality of first photodiodes 1030 according to the second signal and the third signal to generate a fluorescence image signal.

Figure 5:
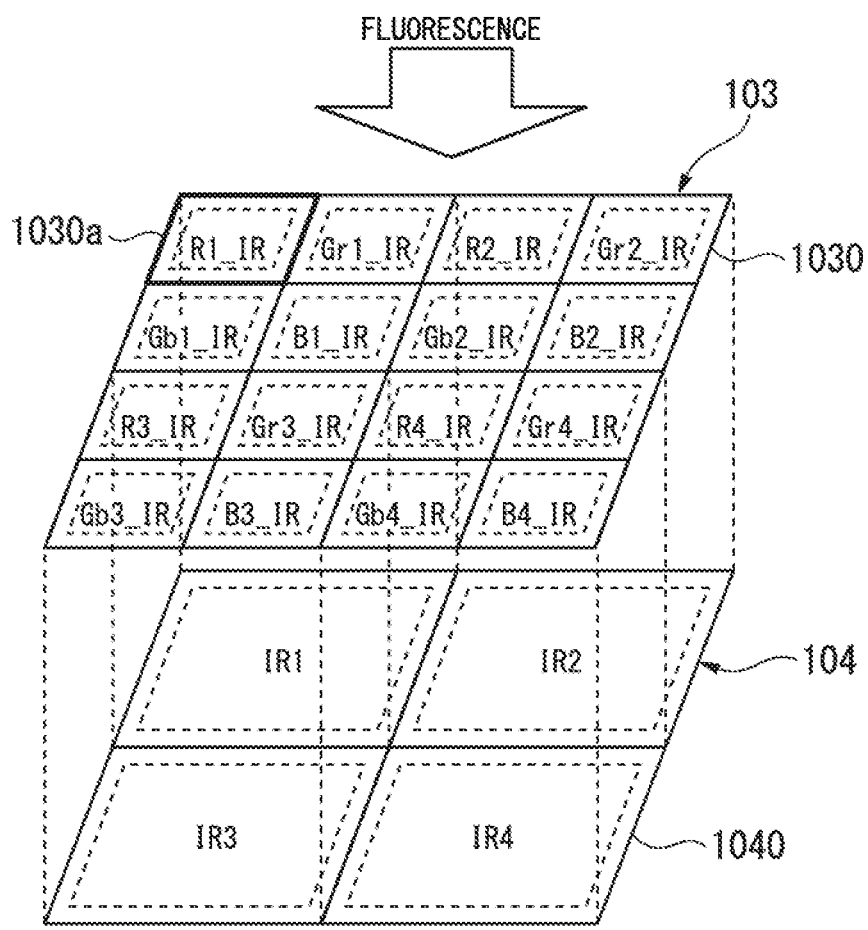
FIG. 5 is a schematic diagram showing a plurality of first photodiodes included in a first image sensor and a plurality of second photodiodes included in a second image sensor in the embodiment of the present invention.

FIG. 5 shows a plurality of first photodiodes 1030 and a plurality of second photodiodes 1040, similar to FIG. 3. In FIG. 5, sixteen first photodiodes 1030 and four second photodiodes 1040 are shown. Values (pixel values) of the second signals generated by the sixteen first photodiodes 1030 and values (pixel value) of the third signals generated by the four second photodiodes 1040 are the same as the values described with reference to FIG. 4.

For example, the arithmetic unit 130 calculates a pixel value S_R1 of the fluorescence image signal corresponding to the first photodiode 1030a using Equation (2). In Equation (2), n1 is a correction parameter. For example, a value of n1 may be a value corresponding to a transmittance of the color filter with respect to the fluorescence.

$$S\_R1 = I1 + R1\_IR \times n1 \quad (2)$$

In Equation (2), a calculation result (R1_IR×n1) of the second signal corresponding to the first photodiode 1030a is added to the third signal (IR1) corresponding to one second photodiode 1040. In Equation (2), the calculation of the second signal is a multiplication calculation. The calculation of the second signal may be a calculation other than the multiplication calculation. A pixel value of the fluorescence image signal corresponding to the first photodiodes 1030 other than the first photodiode 1030a is calculated by the same calculation as in Equation (2).

In the second method of generating a fluorescence image signal, sensitivity of the fluorescence detection is improved. Since the size of the first photodiode 1030 is smaller than the size of the second photodiode 1040, more of the first photodiodes 1030 than the second photodiodes 1040 may be arranged. In the second method of generating the fluorescence image signal, a resolution of the fluorescence image signal is improved, as compared with the first method of generating the fluorescence image signal.

The visible light image signal and the fluorescence image signal may be superimposed. A method of superimposing the visible light image signal with the fluorescence image signal will be described.

A plurality of pixels constituting the visible light image signal according to the signal according to the visible light generated by the plurality of first photodiodes 1030 is defined as the plurality of first pixels. A plurality of pixels constituting the fluorescence image signal according to a signal according to the fluorescence generated by the plurality of first photodiodes 1030 and the plurality of second photodiodes 1040 is defined as the plurality of second pixels. For example, the pixel value of the second pixel is a value calculated using the same calculation as in Equation (1) or (2). In a case where the number of second pixels corresponding to the first pixel is different (is not 1), the arithmetic unit 130 performs calculation according to at least one of the visible light image signal and the fluorescence image signal such that the number matches (becomes 1). The arithmetic unit 130 superimposes the visible light image signal and the fluorescence image signal on which the calculation has been performed.

Figure 6:
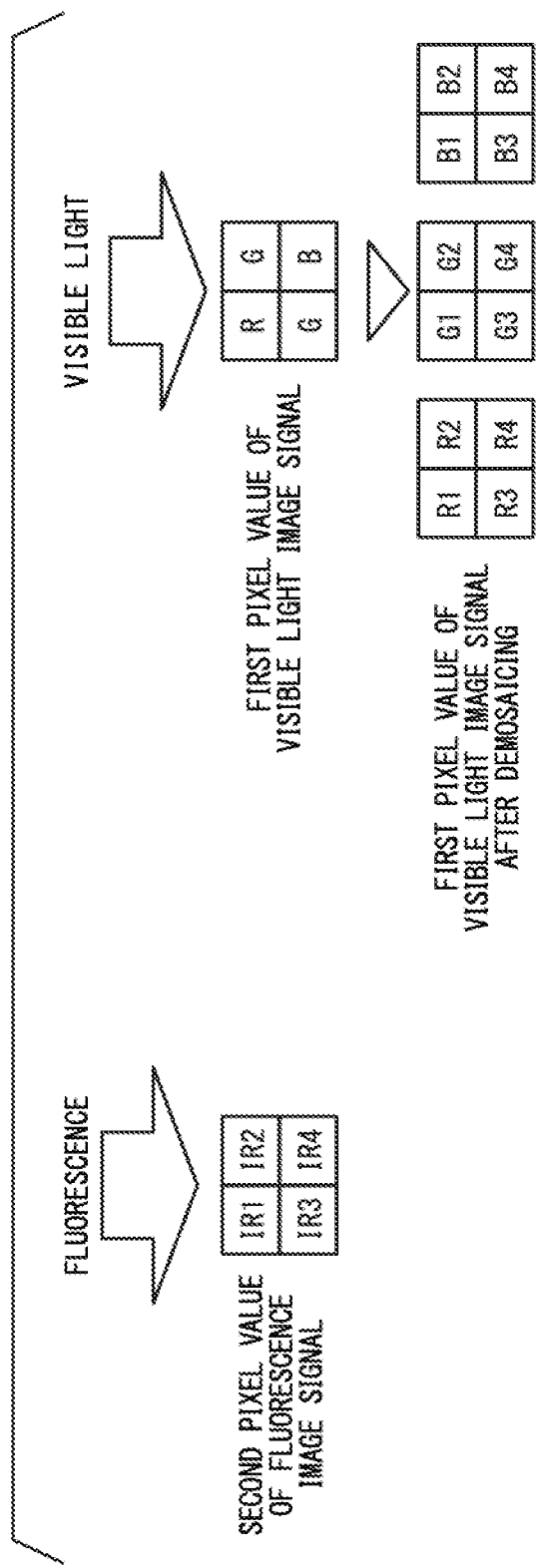
FIG. 6 is a schematic diagram showing pixel values of a visible light image signal and a fluorescence image signal in the embodiment of the present invention.

A first example of superimposing the visible light image signal and the fluorescence image signals will be described. FIG. 6 shows pixel values of the visible light image signal and the fluorescence image signal in the first example of superimposing the visible light image signal and the fluorescence image signal.

In FIG. 6, some of the pixel values of the visible light image signal and the fluorescence image signal are shown as representatives, and not all of the pixel values of the visible light image signal and the fluorescence image signal are shown. In FIG. 6, the pixel values (IR1 to IR4) of four second pixels of the fluorescence image signal are shown. Further, in FIG. 6, pixel values (R, G, G, B) of the tour first pixels of the visible light image signal are shown. The visible light image signal has pixel values of the first pixels of respective colors constituting a Bayer array.

For example, the pixel values of the second pixels of the fluorescence image signal are generated using the second method of generating the fluorescence image signal shown in FIG. 5 and Equation (2). An edge enhancement process may be performed on the fluorescence image signal.

For example, demosaicing may be performed on the visible light image signal. In the demosaicing, the pixel values of the four first pixels shown in FIG. 6 and pixel values of the plurality of first pixels surrounding the four first pixels are used. The pixel value for each color constituting the Bayer array is interpolated by demosaicing. In FIG. 6, the visible light image signal after the demosaicing has been performed includes pixel values (R1 to R4) of the four first pixels corresponding to red (R), pixel values (G1 to G4) of the four first pixels corresponding to green (G), and pixel values (B1 to B4) of the four first pixels corresponding to blue (B). In the visible light image signal after the demosaicing has been performed, the pixel value of the first pixel corresponding to each of the first pixels has a pixel value of each color.

Demosaicing equalizes the number of pixels of the fluorescence image signal corresponding to one pixel of the visible light image signal. White balance processing, an edge enhancement process, or the like may be performed on the visible light image signal after the demosaicing has been performed.

The arithmetic unit 130 superimposes the visible light image signal and the fluorescence image signal after the demosaicing has been performed, to generate a superimposed image signal. For example, the arithmetic unit 130 may calculate pixel values R1', G1', and B1' of the superimposed image signal corresponding to one first pixel using Equations (3) to (5). In Equations (3) to (5), α is a weighting coefficient for determining proportions of the visible light image signal and the fluorescence image signal. In Equations (3) to (5), βr, βg, and βb are coefficients for determining a proportion of the fluorescence image signal for each color. For example, if βr is 0, βg is 1, and βb is 0, the fluorescence is displayed in green in an image according to the superimposed image signal.

$$R1' = \alpha \times R1 + (1-\alpha) \times IR1 \times \beta r \quad (3)$$

$$G1' = \alpha \times G1 + (1-\alpha) \Delta IR1 \times \beta g \quad (4)$$

$$B1'=\alpha \times B1+(1-\alpha)\times IR1\times \beta b \quad (5)$$

A pixel value of the superimposed image signal corresponding to the other first pixels is calculated using the same calculation as in Equations (3) to (5).

By superimposing the visible light image signal and the fluorescence image signal, it is possible to display an emitting position of the fluorescence, that is, a position of a lesion in an image according to the superimposed image signal. Therefore, it is easy for a user viewing the image to identify the position of the lesion.

Figure 7:
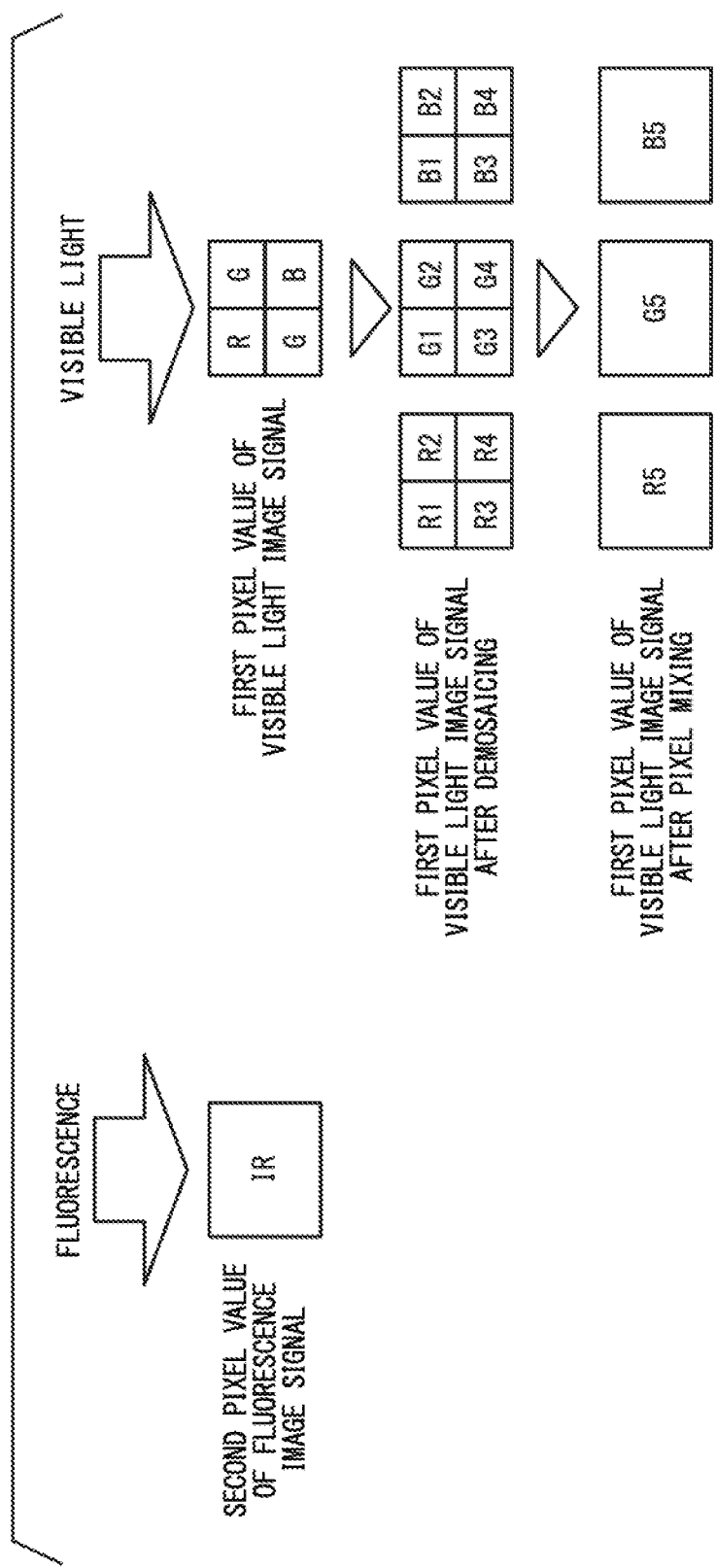
FIG. 7 is a schematic diagram showing pixel values of the visible light image signal and the fluorescence image signal in the embodiment of the present invention.

A second example of superimposing the visible light image signal and the fluorescence image signals will be described. FIG. 7 shows pixel values of the visible light image signal and the fluorescence image signal in the second example of superimposing the visible light image signal and the fluorescence image signal.

In FIG. 7, some of the pixel values of the visible light image signal and the fluorescence image signal are shown as representatives, and not all of the pixel values of the visible light image signal and the fluorescence image signal are shown. In FIG. 7, a pixel value (IR) of one second pixel of the fluorescence image signal is shown. Further, in FIG. 7, pixel values (R, G, G, B) of the four first pixels of the visible light image signal are shown. The visible light image signal has pixel values of the first pixels of respective colors constituting a Bayer array. For example, the pixel values of the second pixels of the fluorescence image signal may be generated using the first method of generating the fluorescence image signal shown in FIG. 4 and Equation (1).

For example, demosaicing is performed on the visible light image signal. In FIG. 7, the visible light image signal after the demosaicing has been performed includes pixel values (R1 to R4) of the four first pixels corresponding to red (R), pixel values (G1 to G4) of the four first pixels corresponding to green (G), and pixel values (B1 to B4) of the four first pixels corresponding to blue (B). In the visible light image signal after the demosaicing has been performed, the pixel value of the first pixel corresponding to each of the first pixels has a pixel value of each color.

For example, pixel mixing is performed on the visible light image signal after the demosaicing has been performed. In the pixel mixing, the pixel values are mixed for the respective colors. In FIG. 7, the visible light image signal after the pixel mixing has been performed includes a pixel value (R5) of the first pixel corresponding to red (R), a pixel value (G5) of the first pixel corresponding to green (G), and a pixel value (B5) of the first pixel corresponding to blue (B).

The numbers of pixels of the fluorescence image signal corresponding to one pixel of the visible light image signal are equalized by pixel mixing.

The arithmetic unit 130 superimposes the visible light image signal and the fluorescence image signal after the pixel mixing has been performed, to generate a superimposed image signal. For example, the arithmetic unit 130 calculates pixel values R5', G5', and B5' of the superimposed image signal corresponding to one first pixel using Equation (6) to (8). In Equations (6) to (8), α is a weighting coefficient for determining proportions of the visible light image signal and the fluorescence image signal. In Equations (6) to (8), βr, βg, and βb are coefficients for determining a proportion of the fluorescence image signal for each color.

$$R5'=\alpha \times R5+(1-\alpha)\times IR\times \beta r \quad (6)$$

$$G5'=\alpha \times G5+(1-\alpha)\times IR\times \beta g \quad (7)$$

$$B5'=\alpha \times B5+(1-\alpha)\times IR\times \beta b \quad (8)$$

A pixel value of the superimposed image signal corresponding to the other first pixels is calculated using the same calculation as in Equations (6) to (8).

Figure 8:
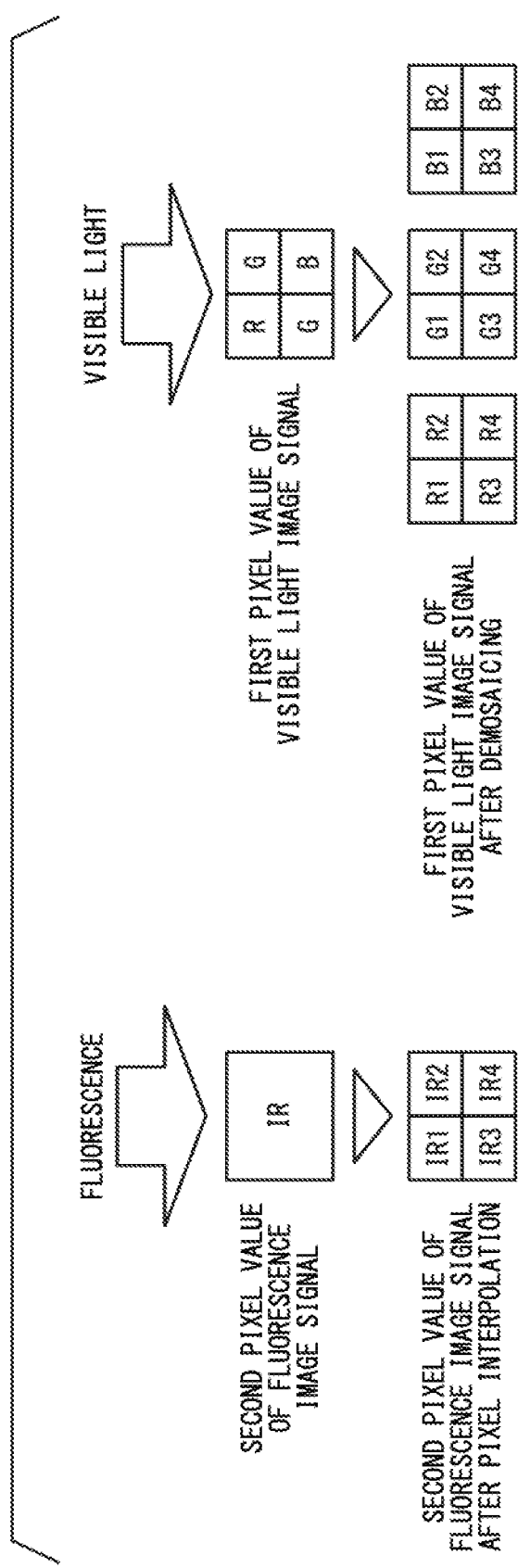
FIG. 8 is a schematic diagram showing pixel values of the visible light image signal and the fluorescence image signal in the embodiment of the present invention.

A third example of superimposing the visible light image signal and the fluorescence image signals will be described. FIG. 8 shows pixel values of the visible light image signal and the fluorescence image signal in the third example of superimposing the visible light image signal and the fluorescence image signal.

In FIG. 8, some of the pixel values of the visible light image signal and fluorescence image signal are shown as representatives, and not all of the pixel values of the visible light image signal and the fluorescence image signal are shown. In FIG. 8, a pixel value (IR) of one second pixel of the fluorescence image signal is shown. Furthermore, in FIG. 8, pixel values (R, G, G, B) of the four first pixels of the visible light image signal are shown. The visible light image signal has pixel values of the first pixels of respective colors constituting a Bayer array. For example, the pixel values of the second pixels of the fluorescence image signal may be generated using the first method of generating the fluorescence image signal shown in FIG. 4 and Equation (1).

For example, pixel interpolation is performed on the fluorescence image signal. In the pixel interpolation, pixel values at positions corresponding to the respective pixels of the visible light image signal are interpolated. For example, a known nearest neighbor interpolation process may be performed. A bilinear or bicubic interpolation process may be performed. In FIG. 8, the fluorescence image signal after the pixel interpolation has been performed includes pixel values (R1 to R4) of the four second pixels. A filtering process or an edge enhancement filtering process in which a visible light image is used as a guide image may be performed on the fluorescence image signal after the pixel interpolation has been performed. For example, a filtering process in which a visible light image is used as a guide image may be a process using a known guided filter or joint bilateral filter. For example, the edge enhancement filtering process may be a process using a known Laplacian filter or a Sobel filter.

For example, demosaicing is performed on the visible light image signal. In FIG. 8, the visible light image signal after the demosaicing has been performed includes pixel values (R1 to R4) of the four first pixels corresponding to red (R), pixel values (G1 to G4) of the four first pixels corresponding to green (G), and pixel values (B1 to B4) of the four first pixels corresponding to blue (B). That is, in the visible light image signal after the demosaicing has been performed, the pixel value of the first pixel corresponding to each of the first pixels has a pixel value of each color.

The arithmetic unit 130 superimposes the visible light image signal after the demosaicing has been performed and the fluorescence image signal after the pixel interpolation has been performed, to generate a superimposed image signal. For example, the arithmetic unit 130 may generate the superimposed image signal through the same calculation as in Equations (3) to (5).

Figure 9:
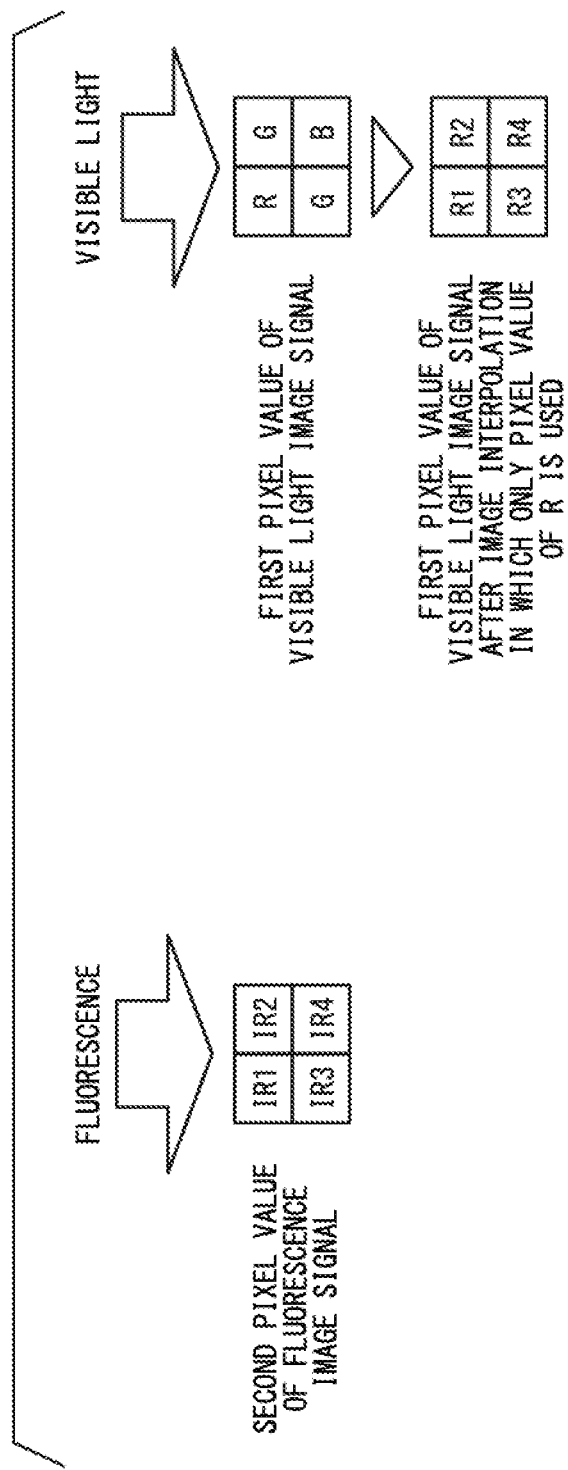
FIG. 9 is a schematic diagram showing pixel values of the visible light image signal and the fluorescence image signal in the embodiment of the present invention.

A fourth example of superimposing the visible light image signal and the fluorescence image signals will be described. The arithmetic unit 130 may use a visible light image signal corresponding to an image in which light having a relatively longer wavelength is emphasized when the visible light image signal and the fluorescence image signal are superimposed. FIG. 9 shows pixel values of the visible light image signal and the fluorescence image signal in the fourth example of superimposing the visible light image signal and the fluorescence image signal.

In FIG. 9, some of the pixel values of the visible light image signal and the fluorescence image signal are shown as representatives, and not all of the pixel values of the visible light image signal and the fluorescence image signal are shown. In FIG. 9, pixel values (IR1 to IR 4) OF FOUR second pixels of the fluorescence image signal are shown. Further, in FIG. 9 pixel values (R, G, G, B) of the four first pixels of the visible light image signal are shown. The visible light image signal has pixel values of the first pixels of respective colors constituting a Bayer array. For example, the pixel values of the second pixels of the fluorescence image signal may be generated using the second method of generating the fluorescence image signal shown in FIG. 5 and Equation (2).

For example, pixel interpolation is performed on the visible light image signal. In the pixel interpolation for the visible light image signal, only the pixel value of the first pixel corresponding to red (R) is used. For example, in the pixel interpolation for the visible light image signal, a bilinear interpolation process may be performed. In FIG. 9, the visible light image signal after the pixel interpolation has been performed has pixel values (R1 to R4) of the four first pixels corresponding to red (R). In the visible light image signal after the pixel interpolation has been performed, the pixel value of the first pixel corresponding to each of the first pixels has a pixel value corresponding to red (R). The visible light image signal after the pixel interpolation has been performed corresponds to an image in which red (R) light having a wavelength longer than that of green (G) and blue (B) light is emphasized.

The numbers of pixels of the fluorescence image signal corresponding to one pixel of the visible light image signal are equalized by pixel interpolation.

The arithmetic unit 130 superimposes the visible light image signal and the fluorescence image signal after the pixel interpolation has been performed, to generate a superimposed image signal. For example, the arithmetic unit 130 calculates pixel values R1', G1' and B1' of the superimposed image signal corresponding to one first pixel using Equation (9) to (11). In Equations (9) to (11), α is a weighting coefficient for determining proportions of the visible light image signal and the fluorescence image signal. In Equations (9) to (11), βr, βg, and βb are coefficients for determining a proportion of the fluorescence image signal for each color.

$$R1'=\alpha \times R1 + (1-\alpha) \times IR1 \times \beta r \quad (9)$$

$$G1'=(1-\alpha) \times IR1 \times \beta g \quad (10)$$

$$B1'=(1-\alpha) \times IR1 \times \beta b \quad (11)$$

A pixel value of the superimposed image signal corresponding to the other first pixels is calculated using the same calculation as in Equations (9) to (11).

In an image in which light having a relatively longer wavelength is emphasized, a region relatively close to a position of a lesion of a blood vessel or the like at a deep position is emphasized. A lesion position is more easily identified by superimposing the visible light image signal and the fluorescence image signal using a visible light image signal corresponding to an image in which light having a relatively longer wavelength is emphasized.

Weights (weighting coefficient α in Equations (3) to (11)) of the visible light image signal and the fluorescence image signal when the visible light image signal and the fluorescence image signal are superimposed can be changed. The degree of emphasis of the fluorescence image with respect to the visible light image changes according to the weights of die visible light image signal and the fluorescence image signal. For example, the weights of the visible light image signal and the fluorescence image signal may change according to the subject. Thus, in the image according to the superimposed image signal, the fluorescence becomes easy to see according to the subject.

The arithmetic unit 130 may determine the weights of the visible light image signal and the fluorescence image signal according to pixel values of the plurality of second pixels of the fluorescence image signal. For example, the arithmetic unit 130 may determine the weights of the visible light Image signal and the fluorescence image signal using Equation (9).

[Equation 1]

$$\alpha = \frac{averge \text{ pixel value of pixel of which pixel value exceeds predetermined value in fluorescence image signal}}{\text{average pixel value of pixel corresponding to above pixel in visible light image signal}} \times n2 \quad (9)$$

In Equation (9), a value obtained by dividing a second average value by a first average value is multiplied by a correction parameter n2. The second average value is an average pixel value of a pixel of which the pixel value in the fluorescence image signal exceeds a predetermined value. The first average value is an average pixel value of a pixel corresponding to a pixel in the visible light image signal. The demosaicing or the like for the visible light image signal equalizes the number of one pixel of the visible light image signal and the number of pixels of the fluorescence image signal corresponding to the number of one pixel of the visible light image signal. Accordingly, the pixel value of the second pixel of each pixel of the fluorescence image signal corresponds to the pixel value of the first pixel of each pixel of the visible light image signal. When the pixel value of the fluorescence image signal corresponding to a certain pixel exceeds a predetermined value, the first average value is calculated from the pixel value of the visible light image signal corresponding to the same pixel.

Thus, the arithmetic unit 130 can determine the weight of the visible light image signal and the fluorescence image signal according to intensity of the fluorescence.

Figure 10:
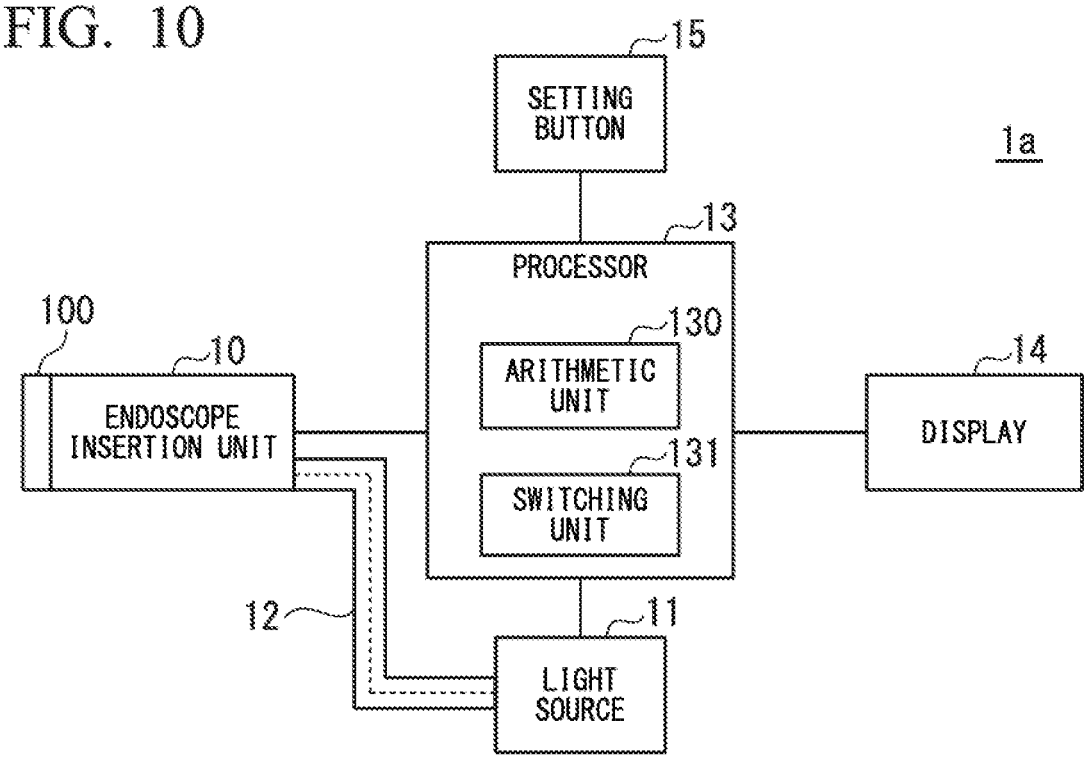
FIG. 10 is a block diagram showing a configuration of an endoscope device according to a modification example of the embodiment of the present invention.

FIG. 10 shows a configuration of an endoscope device 1*a* of a modification example of the embodiment of the present invention. As shown in FIG. 10, the endoscope device 1*a* includes an endoscope insertion unit 10, a light source 11, a light guide 12, a processor 13, a display 14, and a setting button 15. The endoscope insertion unit 10 includes an imaging unit 100 provided in the distal end portion.

A difference between a configuration shown in FIG. 10 and the configuration shown in FIG. 1 will be described. The setting button 15 is operated by a user and receives an instruction from the user. The arithmetic unit 130 may determine the weight of the visible light image signal and the fluorescence image signal according to an instruction from the user.

For points other than the above, the configuration in FIG. 10 is the same as the configuration in FIG. 1.

For example, the arithmetic unit 130 sets the weight of the visible light image signal and the fluorescence image signal to a predetermined value. The arithmetic unit 130 generates a superimposed image signal using the set weight. The display 14 displays an image according to the superimposed image signal. The user operates the setting button 15 while confirming the image displayed on the display 14. Through the operation of the setting button 15, a change in fee weight of the visible light image signal and the fluorescence image signal is instructed. The arithmetic unit 130 may determine the weight of the visible light image signal and the fluorescence image signal according to an instruction from the user. The arithmetic unit 130 generates a superimposed image signal using the determined weight. The display 14 displays an image according to the superimposed image signal.

According the above-mentioned description, fee arithmetic unit 130 can determine the weight of the visible light image signal and die fluorescence image signal according to preference of the user.

A method of switching between visible light and excitation light will be described. In a first method of switching between visible light and excitation light the switching unit 131 performs switching from a first state to a second state with fixed periods, and performs switching from the second state to the first state with fixed periods. The period of switching from the first state to the second state is the same as the period of switching from the second state to the first state. A time in which the first state continues is the same as a time in which the second state continues. The number of frames of imaging performed by the first image sensor 103 and the second image sensor 104 when the endoscope device 1 is in the second state is the same as the number of frames of imaging performed by the first image sensor 103 when the endoscope device 1 is in the first state. In the first state, the subject is irradiated with the visible light. In the second state, the subject is irradiated with the excitation light.

Figure 11:
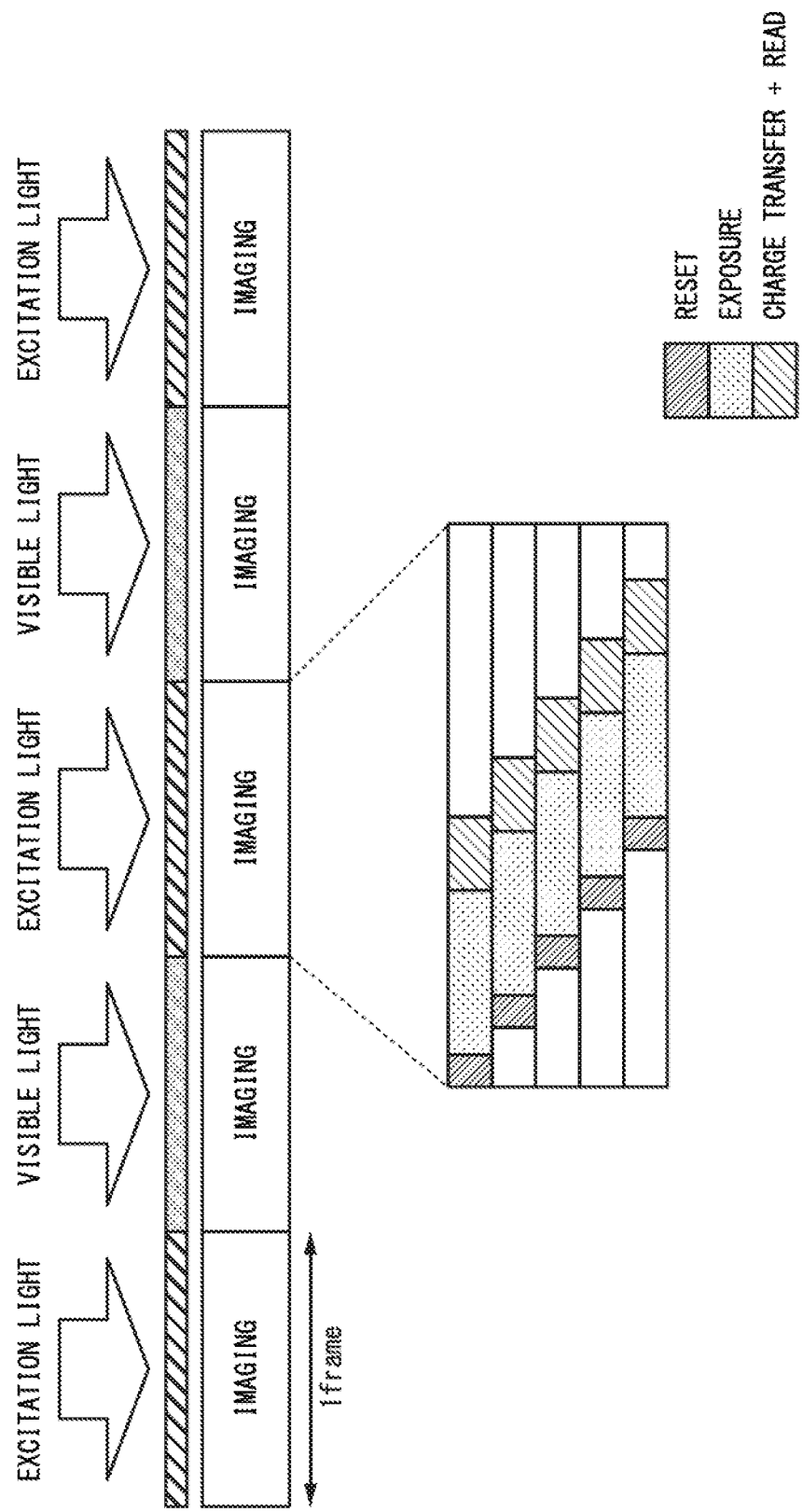
FIG. 11 is a reference diagram showing a state in which switching between the visible light and the excitation light is performed in the embodiment of the present invention.

FIG. 11 shows a state in which the visible light and the excitation light are switched using the first method of switching between the visible light and the excitation light. The first image sensor 103 and the second image sensor 104 perform imaging in fixed flame periods. The visible light and the excitation light are alternately irradiated in synchronization with the imaging by the first image sensor 103 and the second image sensor 104. The visible light and the excitation light are alternately irradiated for each frame of imaging. When the visible light is irradiated, the first image sensor 103 performs imaging. When the visible light is irradiated, the second image sensor 104 may stop imaging. When the excitation light is irradiated, the first image sensor 103 and the second image sensor 104 perform imaging.

In FIG. 11, one frame of imaging is enlarged and shown. In the one frame of the image, control of imaging is sequentially performed for respective rows of the array of the plurality of first photodiodes or the plurality of second photodiodes. The control of the imaging of one row is performed as follows. The first photodiodes or the second photodiodes are reset. Then, exposure is performed in the first photodiodes or the second photodiodes. Then, charge accumulated in the first photodiodes or the second photodiodes is transferred to a storage unit such as a capacitor, and then, the signal is read from the storage unit.

In the first method of switching between the visible light and the excitation light, the visible light and the excitation light are switched in synchronization with one frame of imaging. A deviation of timing between capturing of the visible light image and capturing of the fluorescence image is only one frame. It is possible to acquire the visible light image and the fluorescence image captured at substantially the same time. As a result, the amount of a deviation of the subject between the visible light image and the fluorescence image can be minimized. The user can easily perform a comparison between the visible light image and the fluorescence image. In a case where the visible light image signal and the fluorescence image signal are superimposed, the user may easily compare a portion according to the visible light, image signal with a portion according to the fluorescence image signal in an image according to the superimposed image signal.

In a second method of switching between the visible light and the excitation light, the switching unit 131 performs switching from a first state to a second state with fixed periods, and performs switching from the second state to the first state with fixed periods. The period of switching from the first state to the second state is the same as the period of switching from the second state to the first state. A time in which the first state continues is different from a time hi which the second state continues. The number of frames of imaging performed by the first image sensor 103 and the second image sensor 104 when the endoscope device 1 is in the second state is larger than the number of frames of imaging performed by the first image sensor 103 when the endoscope device 1 is in the first state. In the first state, the subject is irradiated with the visible light. In the second state, the subject is irradiated with the excitation light.

Figure 12:
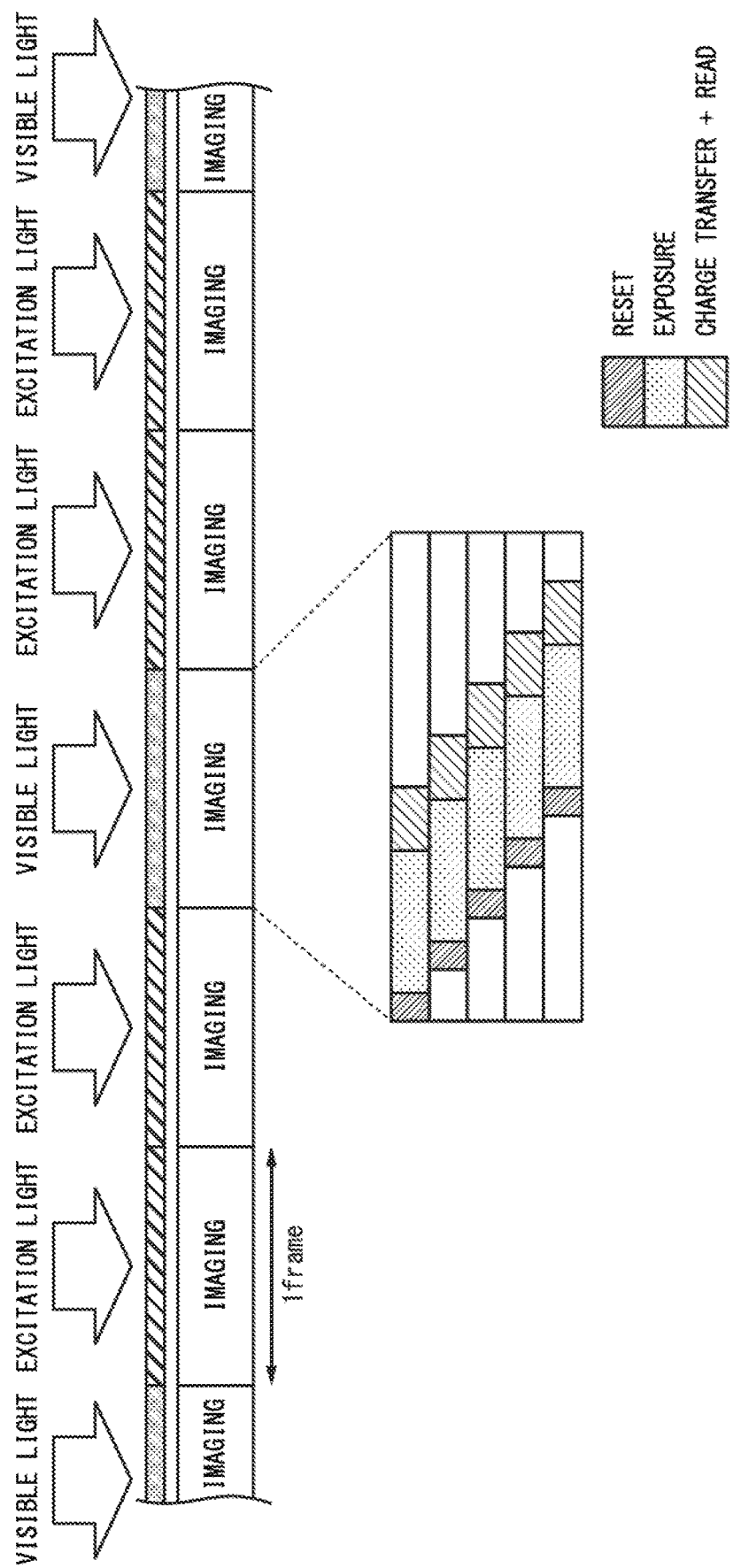
FIG. 12 is a reference diagram showing a state in which switching between the visible light and the excitation light is performed in the embodiment of the present invention.

FIG. 12 shows a suite in which the visible light and the excitation light are switched using the second method of switching between the visible light and the excitation light. The first image sensor 103 and the second image sensor 104 perform imaging in fixed frame periods. The visible light is irradiated in one frame of imaging. The excitation light is irradiated in two continuous frames of imaging. The visible light and the excitation light are alternately irradiated. That is, the visible light is irradiated in one of three continuous frames of imaging, and the excitation light is irradiated in the two other frames. When the visible light is irradiated, the first image sensor 103 performs imaging. When the visible light is irradiated, the second image sensor 104 may stop imaging. When the excitation light is irradiated, the first image sensor 103 and the second image sensor 104 perform imaging.

In FIG. 12, one frame of imaging is enlarged and shown. One frame of imaging in FIG. 12 is the same as one frame of the image in FIG. 11.

In the second method of switching between the visible light and the excitation light, switching between the visible light and the excitation light may be performed so that an irradiation time of the excitation light in a predetermined time is longer than an irradiation time of the visible light. A period in which the irradiation of the visible light continues is not limited to two continuous frames of imaging. The period in which the irradiation of the visible light continues may be three or more continuous frames of imaging. Further, a period in which the irradiation of the excitation light continues is not limited to one frame of imaging. The period in which the irradiation of the excitation light continues may be two or more continuous frames of imaging.

In the second method of switching between the visible light and the excitation light, a sensitivity of fluorescence detection is improved without greatly impairing simultaneity of acquisition of the visible light image and the fluorescence image.

In a third method of switching between the visible light and the excitation light, the switching unit 131 performs switching from a first state to a second state with fixed periods, and performs switching from the second state to the first state with fixed periods. The period of switching from the first state to the second state is the same as the period of switching from the second state to the first state. A time in which the first state continues is different from a time in which the second state continues. A frame length of imaging performed by the first image sensor 103 and the second image sensor 104 when the endoscope device 1 is in the second state is larger than a frame length of imaging performed by the first image sensor 103 when the endoscope device 1 is in the first state. In the first state, the subject is irradiated with the visible light. In the second state, the subject is irradiated with the excitation light.

Figure 13:
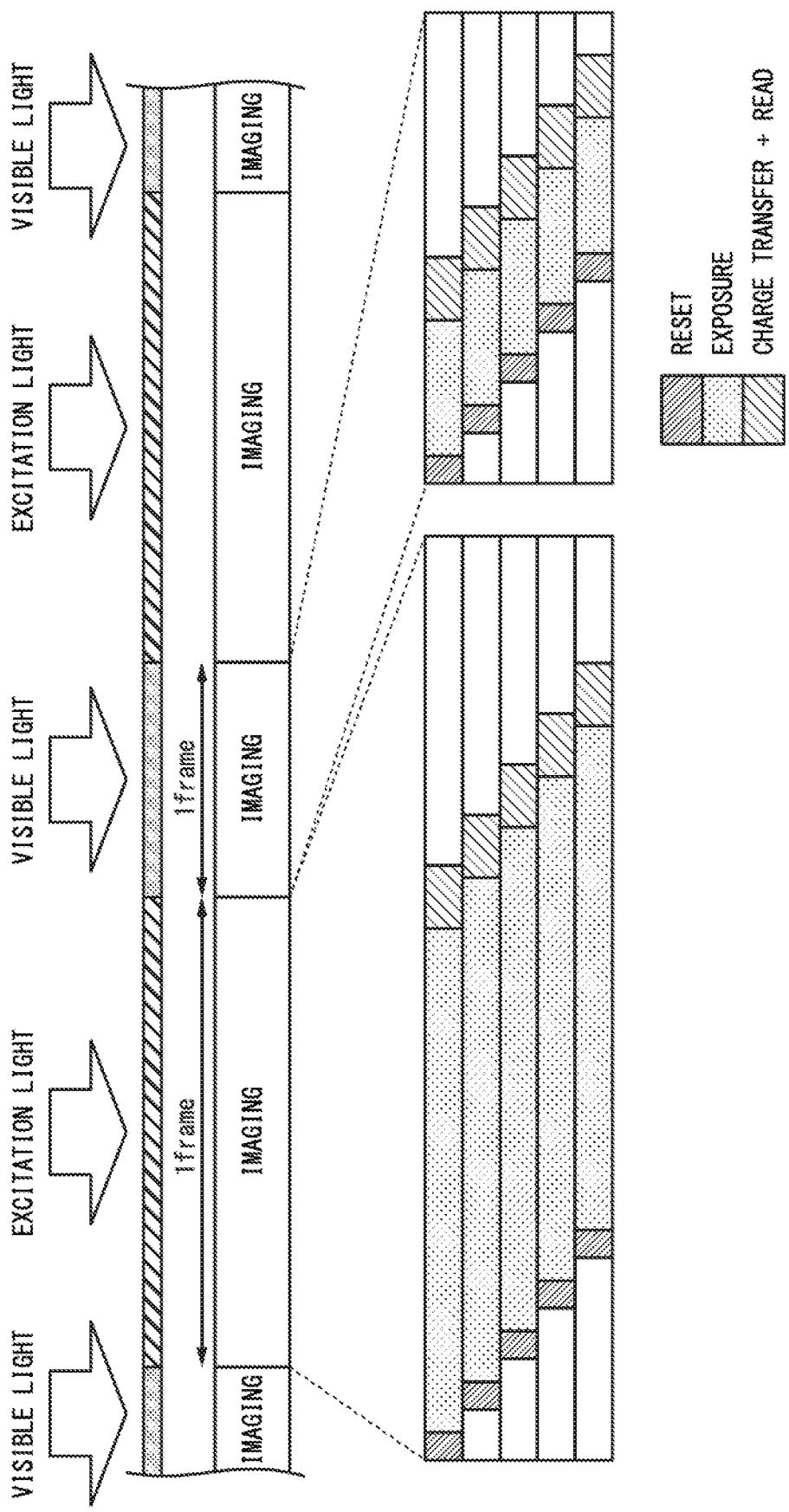
FIG. 13 is a reference diagram showing a state in which switching between the visible light and the excitation light is performed in the embodiment of the present invention.

FIG. 13 shows a state in which the visible light and the excitation light are switched using the third method of switching between the visible light and the excitation light. One frame of imaging when the excitation light is irradiated is longer than one frame of imaging when the visible light is irradiated. The visible light and the excitation light are alternately irradiated in synchronization with the imaging by the first image sensor 103 and the second image sensor 104. The visible light and the excitation light are alternately irradiated for each frame of imaging.

As described above, a length of one frame of imaging is different between the first state in which the visible light is irradiated and the second state in which the excitation light is irradiated. An irradiation time of the visible light and an irradiation time of the excitation light are different. When one frame of imaging when the excitation light is irradiated is longer than one frame of imaging when the visible light is irradiated, the irradiation time of the excitation light is longer than the irradiation time of the visible light. When the visible light is irradiated, the first image sensor 103 performs imaging. When the visible light is irradiated, the second image sensor 104 may stop imaging. When the excitation light is irradiated, the first image sensor 103 and the second image sensor 104 perform imaging.

In FIG. 13, one frame of imaging when the excitation light is irradiated and one frame of imaging when the visible light is irradiated are enlarged and shown. A procedure of an operation in imaging by the first image sensor 103 and the second image sensor 104 is the same as the procedure described with reference to FIG. 11. However, an exposure period is different between imaging when the excitation light is irradiated and imaging when the visible light is irradiated. As shown in FIG. 13, the exposure period in imaging when the excitation light is irradiated is longer than the exposure period in imaging when the visible light is irradiated.

In the third method of switching between the visible light and the excitation light, a sensitivity of fluorescence detection is improved without greatly impairing simultaneity of acquisition of the visible light image and the fluorescence image.

A sensitivity of the second image sensor 104 to near-infrared light may be higher than a sensitivity of the first image sensor 103 to near-infrared light. For example, for the first image sensor 103, a back side illumination (BSI) type image sensor that has a low sensitivity to near-infrared light, that is, for which it is relatively easy for near-infrared light to be transmitted may be used. For example, for the second image sensor 104, a front side illumination (FSI) type image sensor that has a very high sensitivity to near-infrared light may be used.

The wavelength of the excitation light and the fluorescence is in a wavelength band of near-infrared light. By increasing the sensitivity of the second image sensor 104 to near-infrared light, the sensitivity of fluorescence detection is improved.

The endoscopic device of each aspect of the present invention may not have a configuration corresponding to at least one of the light guide 12, the display 14, and the setting button 15.

According to the embodiment of the present invention, the endoscope device 1 includes the light source 11, the endoscope insertion unit 10 including the imaging unit 100, the arithmetic unit 130, and the switching unit 131. The imaging unit 100 includes the excitation light cut filter 102, the first image sensor 103, and the second image sensor 104.

In the embodiment of the present invention, it is possible to achieve both of a small size for the imaging unit 100 and high accuracy detection of the fluorescence and the visible light.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. An endoscope device, comprising:
   a light source configured to generate visible light and excitation light;
   an imaging unit; and
   a processor having an arithmetic circuit and a switching circuit, wherein
      the arithmetic circuit is configured to generate a visible light image signal according to a first signal and a fluorescence image signal according to a second signal and a third signal; and
      the switching circuit is configured to switch between a first state and a second state, wherein the light source generates the visible light for irradiating a subject in the first state and the light source generates the excitation light for irradiating the subject in the second state,
   wherein the imaging unit includes
      an excitation light cut filter configured to transmit the visible light reflected by the subject when the subject is irradiated with the visible light, transmit fluorescence generated when the subject is irradiated with the excitation light, and filter out the excitation light reflected by the subject when the subject is irradiated with the excitation light;
      a first image sensor including a plurality of first photodiodes, each of the plurality of first photodiodes being provided with a corresponding color filter, and the plurality of the first photodiodes being configured to generate the first signal according to the visible light transmitted through the excitation light cut filter and the second signal according to the fluorescence transmitted through the excitation light cut filter; and
      a second image sensor including a plurality of second photodiodes, the plurality of the second photodiodes being configured to generate the third signal according to the fluorescence transmitted through the plurality of first photodiodes,
   wherein two or more of the photodiodes and one of the plurality of second photodiodes overlap each other such that the fluorescence transmitted through the two or more of the first photodiodes is incident on the one of the plurality of second photodiodes, and
   wherein the arithmetic circuit is configured to generate the fluorescence image signal by calculating pixel values corresponding to respective regions of the plurality of the second photodiodes according to the third signal and the second signal.

2. The endoscope device according to claim 1, wherein a size of each of the plurality of second photodiodes is larger than a size of each of the plurality of first photodiodes.

3. The endoscope device according to claim 1, wherein the arithmetic circuit is configured to perform a calculation according to at least one of the visible light image signal and the fluorescence image signal such that a number of pixels in the fluorescence image signal corresponding to a pixel in the visible light image signal becomes one when the number of pixels in the fluorescence image signal corresponding to the one pixel in the visible light image signal is different from one, and the arithmetic circuit is configured to superimpose the visible light image signal and the fluorescence image signal on which the calculation is performed.

4. The endoscope device according to claim 3, wherein weights of the visible light image signal and the fluorescence image signal when the visible light image signal and the fluorescence image signal are superimposed are changeable.

5. The endoscope device according to claim 4, wherein the arithmetic circuit is configured to determine the weights according to the pixel value of the fluorescence image signal.

6. The endoscope device according to claim 4, wherein the arithmetic unit arithmetic circuit is configured to determine the weights according to an instruction from a user.

7. The endoscope device according to claim 3, wherein the arithmetic unit arithmetic circuit is configured to use the visible light image signal corresponding to an image in which light having a relatively longer wavelength is emphasized when the visible light image signal and the fluorescence image signal are superimposed over each other.

8. The endoscope device according to claim 1, wherein the switching circuit is configured to switch from the first state to the second state with a fixed period, and switch from the second state to the first state with the fixed period, and a number of frames of imaging performed by the first image sensor and the second image sensor when the endoscope device is in the second state is the same as a number of frames of imaging performed by the first image sensor when the endoscope device is in the first state.

9. The endoscope device according to claim 1, wherein the switching circuit is configured to switch from the first state to the second state with a fixed period, and switch from the second state to the first state with the fixed period, and a number of frames of imaging performed by the first image sensor and the second image sensor when the endoscope device is in the second state is larger than a number of frames of imaging performed by the first image sensor when the endoscope device is in the first state.

10. The endoscope device according to claim 1, wherein the switching circuit is configured to switch from the first state to the second state with a fixed period, and switch from the second state to the first state with the fixed period, and a frame length of imaging performed by the first image sensor and the second image sensor when the endoscope device is in the second state is longer than a frame length of imaging performed by the first image sensor when the endoscope device is in the first state.

11. The endoscope device according to claim 1, wherein a sensitivity of the second image sensor to near-infrared light is higher than a sensitivity of the first image sensor to near-infrared light.

* * * * *